US00PP12791P2

(12) United States Plant Patent
Patra et al.

(10) Patent No.: US PP12,791 P2
(45) Date of Patent: Jul. 23, 2002

(54) **NOVEL, HIGH YIELDING STABLE *MENTHA ARVENSIS* PLANT NAMED 'DAMROO'**

(75) Inventors: Nirmal Kumar Patra; Sushil Kumar; Suman Preet Singh Khanuja; Ajit Kumar Shasney; Alok Kalra; Herikesh Bahadur Singh; Hemendra Pratap Singh; Ved Ram Singh; Hasan Tanveer; Nareshwar Mengi; Dharmendra Kumar Rajput; Mahendra Singh Negi; Neeraj Kumar Tyagi; Paltoo Ram; Vijay Pal Singh; Ram Sajeevan Shukla; Birendra Kumar; Jitendra Pratap Singh; Raja Ram; Vijay Kumar; Shiv Ram Sharma, all of Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/537,508

(22) Filed: Mar. 29, 2000

(51) Int. Cl.[7] ..... A01H 5/00

(52) U.S. Cl. ..... Plt./259

(58) Field of Search ..... Plt./259

*Primary Examiner*—Bruce R. Campell
*Assistant Examiner*—June Hwu
(74) *Attorney, Agent, or Firm*—Finnegan, Henderson, Farabow, Garrett & Dunner, L.L.P.

(57) ABSTRACT

A novel *Mentha arvensis* mint population-variety 'Damroo' capable of producing viable seeds and phenotypically homogeneous seed-derived plant population when cross pollinated within its own population and capable of high yield of mint oil.

4 Drawing Sheets

FIELD OF INVENTION

The present invention is related to the development of a stable and high yield mint plant called 'Damroo' capable of producing viable seeds and phenotypically homogeneous seed derived population. More particularly, the invention relates to a high essential oil yielding variety 'Damroo' capable of producing viable seeds and therefore useful as a regular seed-source for raising homogenous seedling populations, an essential prelude to raising an ideal transplanted mint crop. The mint crop can be grown by transplantation after wheat cultivation, instead of cultivating it as main crop in place of wheat, a long sought wise option for cultivating mint without affecting the cultivation of the staple cereal wheat. 'Damroo' owing to its stability in seed-grown population for all morpho-physiological attributes, advances the development of sustained yields.

BACKGROUND OF THE INVENTION

Menthol mint is grown in tropical and sub-tropical agro-climates for its essential oil. The oil, besides being widely used for producing menthol and the by-product dementholised oil (DMO), also finds uses in pharmaceutical and cosmetic industries. Menthol has a cooling, refreshing aroma and antiseptic properties. The menthol derivatives are also used in flavouring confectionery and cigarettes. Indeed, profitability in menthol mint is motivating the crop growers to grow it widely, even at the expense of conventional crops like wheat, sugarcane, and vegetables. This has been a metter of concern, especially regarding the fate of wheat crop in the Indogangetic plains of India. Wheat being a major staple food, significant reduction in wheat cultivation in exchange for cultivation of menthol mint may lead to the eventual wheat shortages. One pragmatic solution lies in the development of more efficient agrotechnologies for mint crops, so that crop growers would need only 50% of the area used presently and be able to cultivate both the crops. To the plant breeder, it means that he should put efforts to evolve varieties having doubled productivity. The Central Institute of Medicinal and Aromatic Plants (CIMAP), Lucknow, India, having made large efforts in this regard, has witnessed fascinating success in developing high yielding varieties with much impressive yield improvement, of which the variety 'Kosti' (U.S. Ser. No. 09/145,546) having double oil productivity over earlier widely grown familiar variety 'Shivalik' (unpatented), is now enjoying the highest adorations of the crop growers.

Besides evolving the productive varieties, another wise option, which has long been proposed and initiated, but is yet to be much improved for its wide acceptance, is to resort to cultivating menthol mint as a late transplanted crop from April to July after wheat cultivation instead of cultivating it as major crop during February to June, when wheat is grown. In cultivating menthol mint as a transplanted crop, to depend upon the late planted sucker-grown nursery (but not seed-grown nursery) during the advent of summer (or spring) has been a general practice in raising transplanted mint crops during summer. However, with such a sucker-grown nursery exclusively providing the over matured hardy plants for transplanting, the plant growth as well as productivity in the transplanted mint crop, with very rare exceptions, are always very low. Seed-progeny research over the last five years has given an a priori clue that seeds can be grown in a nursery during winter months and young seedlings can be made available during summer months (April–May) for raising the transplanted mint crop. Keeping this in mind, attempts were made during 1994–1996 to extensively research into the open pollinated seed progenies of the familiar variety 'Shivalik' (unpatented) to explore the possibility of inventing a stable producing genotype.

OBJECTIVES

The main object of the invention is to develop a stable and high yielding mint plant capable of producing viable seeds and phenotypically homogeneous seed derived plant population.

Another object of the invention is to identify and develop a stable seed-producing population variety of *M. arvensis* plant which, as generally known, does not set seeds under selfing conditions (except in very rare cases).

Yet another object of the invention is to develop plants that can provide homogeneous seeds even under cross pollination conditions within its own plant population.

Still another object is to develop mint plants capable of high yield of mint oil.

Another object of the invention is to develop a stable seed producing mint variety with high mint oil yield and menthol content.

Yet another object of the invention is to develop a novel mint variety that has improved disease resistance, higher biomass, high oil yield, and high seed yield.

SUMMARY OF THE INVENTION

To meet the above objectives, the present invention provides a novel *Mentha arvensis* mint population-variety 'Damroo' capable of producing viable seeds and phenotypically homogeneous seed-derived plant population when cross pollinated within its own population and capable of high yield of mint oil.

DETAILED DESCRIPTION

Accordingly, the invention provides a new and distinct variety 'Damroo' having the following new combination of characteristics as compared to conventional known varieties of *M. arvensis*, said plant having the following combination of characteristics:

(a) a plant height of about 100–110 cm;
(b) dark greenish leaves, whitish to whitish-purple flowers, and branching providing pyramidal habit;
(c) a high seed yield, compared to all other existing varieties of menthol mint;
(d) better tolerance to leaf spot, rust, and powdery mildew;
(e) a yield of essential oil containing 78–80% menthol and 12–17% isomenthone;
(f) a yield of seeds in the range of about 90–96 kg/hectare against 30 kg/hectare in 'Shivalik' (unpatented); and
(g) capable of retaining homogeneity in population for plant traits, despite out-crossing within the population.

In an embodiment, the invention also provides seeds produced by the novel plant 'Damroo.'

In yet another embodiment, the invention provides progenies produced by the novel plant 'Damroo.'

The seed producing variety 'Damroo' is the selection from the existing variety of mint plant called 'Shivalik' (unpatented).

The invention is described in detail herein below.

BREEDING HISTORY

Figure 1:
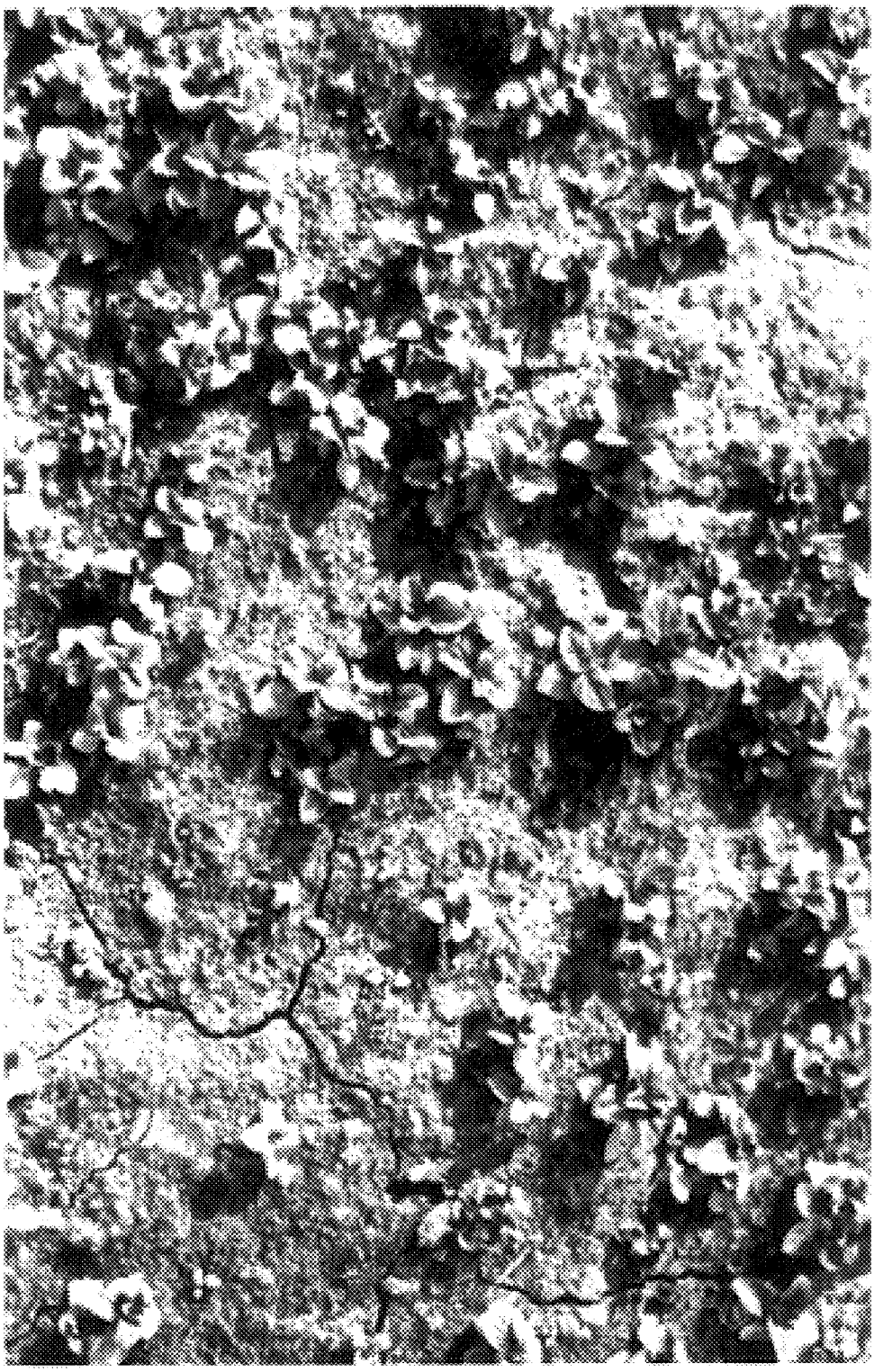
FIG. 1 represents the seedlings of the variety 'Damroo' (*Mentha arvensis*).

The seed producing variety 'Damroo' developed in this invention is an outcome of a strategic approach of raising a large population of open pollinated seed progenies to serve as an original gene pool of a specific menthol mint variety, identifying the variant (spontaneous recombinant) with the desirable traits (higher oil seed yield and high oil productivity), progeny-testing of the variant for phenotypic segregation, creating homogeneous progeny of the variant via repeated, intentional, natural out-crossing between the phenotypically identical progenies, selections in the progeny generations only for the "likes" and appraisals of the homogeneous progeny population (i.e. population variety 'Damroo') against existing standard cultivars (controls) for the desirable plant traits. 'Damroo' cultivar development, propagation, and testing were performed in field plots in Lucknow, India, and at Field Station Pantnagar, in Pantnagar, India. Among the existing menthol mint cultivars, 'Shivalik' (unpatented) was the best genotype for setting viable seeds under out-crossing, and was identified as the starting genetic material for raising the open pollinated seed progenies for the genetical selections. The Applicants collected about 10 gms of open pollinated minute seeds in bulk from a total of randomly selected 15 morphologically elite plants of 'Shivalik' (unpatented) grown in a large commercial field measuring a total cropping area of five hectares during first week of July 1994. The bulked seeds from the 15 plants were grown in a well prepared raised nursery bed during November 1994. Of the total 250 seedlings obtained from the nursery and subsequently transplanted in a separate field during April 1995, 222 survived to provide as original gene pool for exercising the genetical selections. Among the 222 plants, a total of only 14 plants showing profuse flowering, was selected and their seeds were separately collected during June 1995. The seed weight in the selected plants ranged from 0.50 to 2.50 gms, the highest seed weight (2.50 gms) being recorded in the Sel.4-6-125 which was alike with its mother plant for deep green leaf colour, but excelled the latter as well as the rest 13 selected plants for growth habit and flowering branches. In order to avoid the possible chances of losing the material through natural mortality, all the 14 selected plants were separately vegetatively multiplied by their underground suckers and maintained mainly as buffer clonal stocks marking them as the "fixed first ($S_0$) generation-hybrid" progenies (fixed for all plant traits by vegetative propagation). The open pollinated seeds of June 1995 were grown in nursery beds during November 1995. The seedlings were maintained in nursery beds with proper care till the $6^{th}$ April, 1996—i.e. until the time when they attained the fifth leaf-stage and the average height of 15 cm (as against the sucker-grown mature plants of at least 30 cm which are generally used for raising the transplanted mint crop). The number of seedlings in the 14 selections greatly varied with the range: 35 (in the Sel.8-4-125) to as high as 762 (in Sel.4-6-125). FIG. 1 represents of the seedling of the variety 'Damroo' (*Mentha arvensis*). It represents seed-nursery of the mother variety 'Shivalik' (unpatented), showing sparsely grown seedling.

A point of much interest arose with our study of segregation (heterogeneity). The plant traits in the seedling population of the 14 selected plants are supposed to show heterogeneity in the seed-progeny, under the assumption of the generally accepted view of invariable genetic segregation in an open pollinated seed progeny of heterozygous perennial plants (*M. arvensis*, though grown as annual, is indeed perennial because it is grown vegetatively by suckers). However, none of the 14 selections revealed any segregation, with the very rare exceptions of 1 to 6 variant plants exhibiting weak growth habit and somewhat different leaf colour (light green against dark green of the progenitor and shape (globalur/bushy against pyramidal of the progenitor), revealed any segregation. Unexpectedly, all the open pollinated seed-progeny-populations ($S_1$ populations) of the selections, including that of the Sel.4-6-125, which had supremacy over others for growth performance, were identical to their progenitors for morphology. The grown-up seedling of all the selections were separately transplanted in isolated blocks on $7^{th}$ April, 1996, leaving their off-type variants to facilitate the natural out-crossings between the "likes" within each selection (the open pollinated seed-progeny population).

Attempts were made to collect selfed and out-crossed seeds of all the selections. It is worth while to record that none of them except Sel.4-6-125, set seeds under controlled selfing, despite all of them nevertheless setting seeds under out-crossings between the "likes." The seeds were separately collected during July–August 1996 and subsequently grown in nursery as the third generation populations ($S_2$ populations). The number of raised seedlings in $S_2$ populations ranged from 68 (in Sel.8-12-125) to 688 (in Sel.4-6-125). Thus, once again the selection 4-6-125, came out as the best among 14 selections for viable seed productivity as axiomatic to its ascertained ability to give the maximum seedlings. The seedlings of $S_2$ populations were transplanted in the similar way as done for $S_1$ generation, during first week of April 1997. The comparative results of morpho-physiological fitnesses of the $S_2$ populations were completely consistent with those of $S_0$ and $S_1$ populations. Despite the "within the population" out-crossings in $S_1$ populations, none of the derived $S_2$ populations including that of Sel.4-6-125 revealed segregation for plant traits except each being identical with its progenitor population ($S_1$). Interestingly, both the selfed and out-crossed $S_2$ populations of Sel.4-6-125, besides retaining their morphological similarity with their progenitor population ($S_1$), did not differ from each other for morphology.

Figure 2:
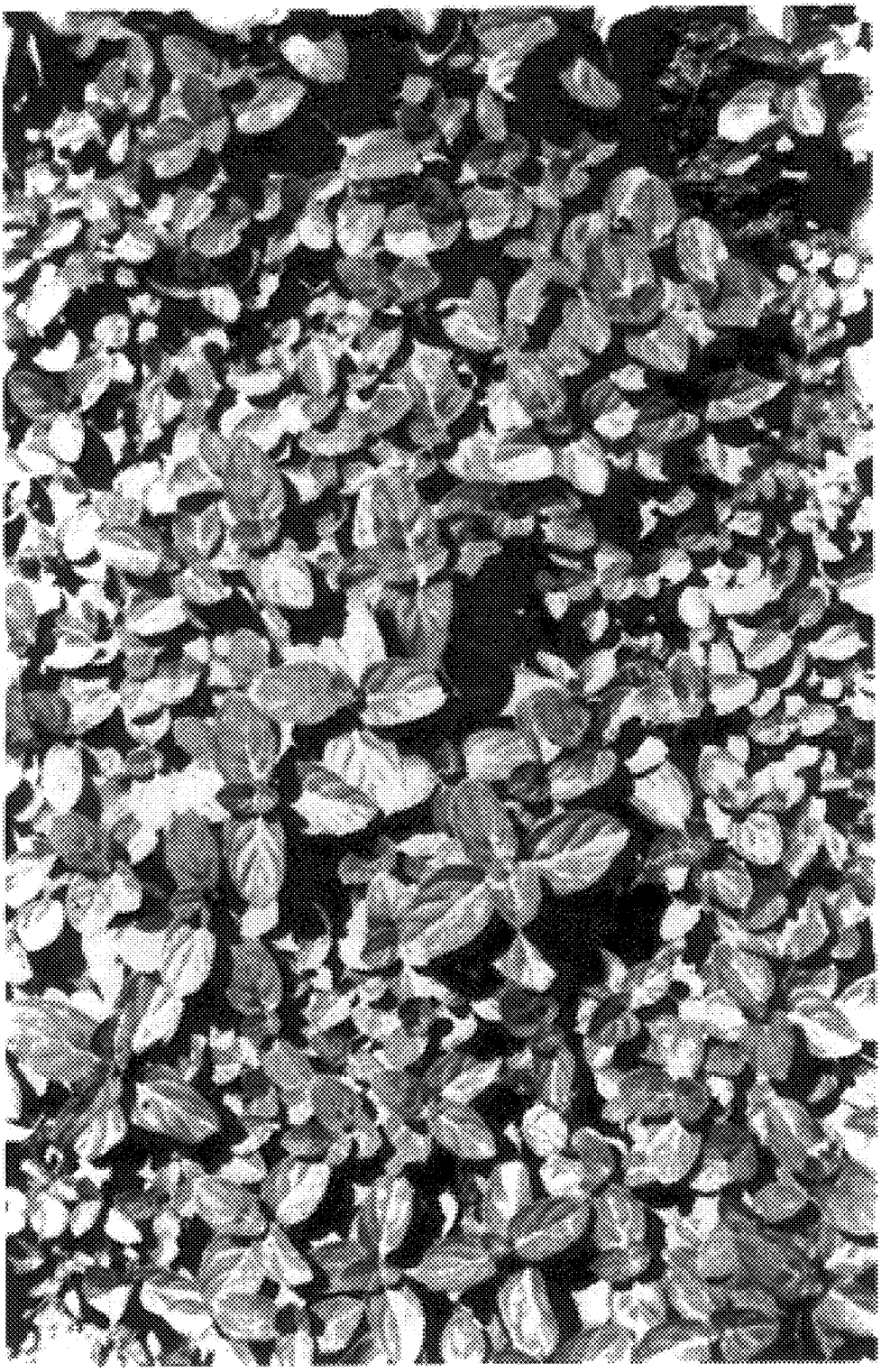
FIG. 2 represents a seed nursery of the variety 'Damroo,' showing the profuse growth of seedlings.
Figure 3:
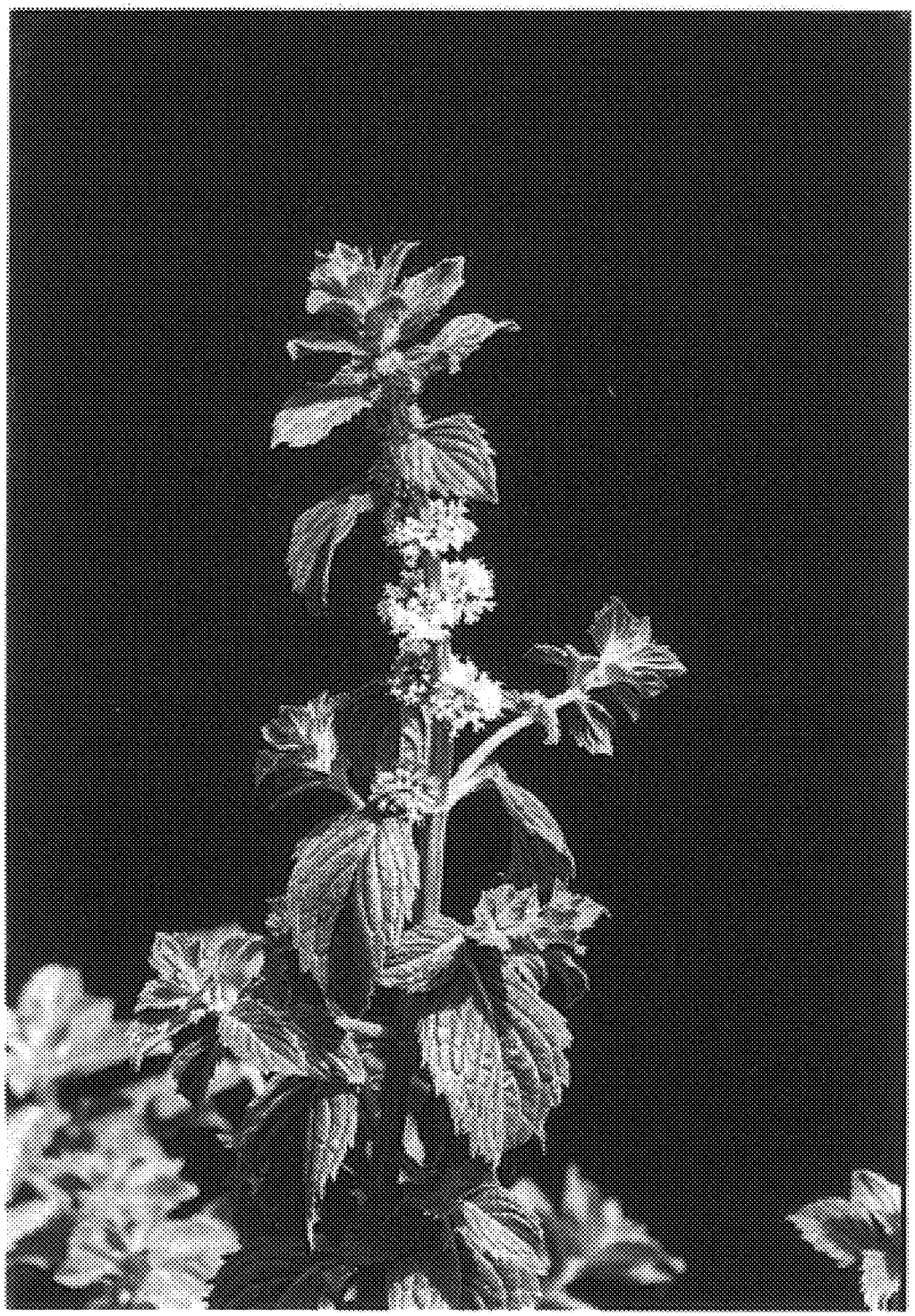
FIG. 3 represents a single 'Damroo' plant during flowering.
Figure 4:
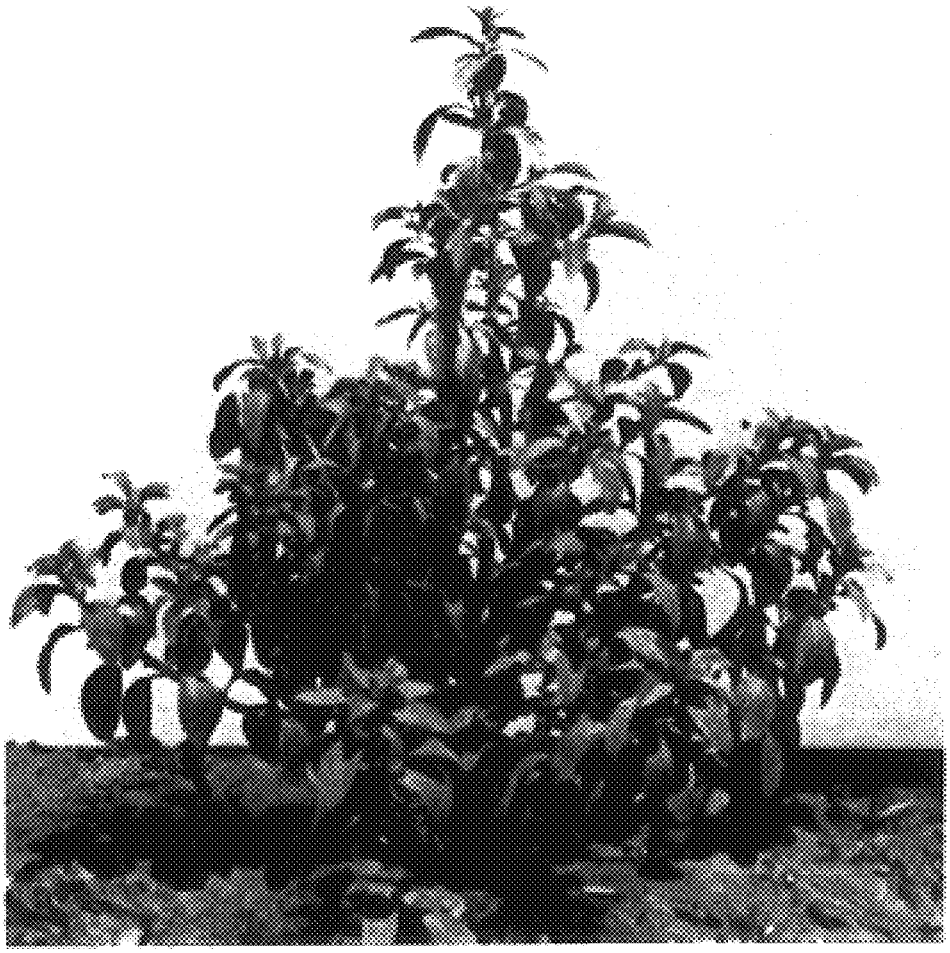
FIG. 4 represents pyramidal plant habit of 'Damroo'.

From the results of the $S_0$, $S_1$, and $S_2$ populations, it was evident that Sel.4-6-125, unlike the other 13 selections, has both selfing, and out-crossing systems, coupled with the additional genetic mechanism for retaining its maternal traits, perhaps through apomixis over generations, provided its population in different generations comprises morpho-physiologically identical individuals. It appeared likely that all our developed selections except Sel.4-6-125 are perhaps obligate apomicts which, apart from having only cross fertility, do not have self compatibility leading to no seed settling in their selfing. Sel.4-6-125, later named as the population-variety 'Damroo', owing to its superiority over the others for seed yield and population stability for all morpho-physiological fitnesses, was attempted for its further assessment against all standard varieties for productivity. In fact, the consistent results of $S_0$ and $S_1$ seedling populations of 'Damroo' regarding its morpho-physiological stability, led us to conduct its preliminary yield trial (PYT) during 1997–1998. Its pilot scale yield trial was conducted during 1998–1999, on the basis of the consistent stability results of the $S_0$, $S_1$, and $S_2$ populations. FIG. 2 represents a seed nursery of the variety 'Damroo' showing profuse growth of seedlings. Similarly, FIG. 3 represents a field of 'Damroo' showing its synchronous flowering. FIG. 4 represents the canopy of 'Damroo'. Tables 1 and 2 represent the performance of 'Damroo' in comparison with the mint varieties 'Shivalik' (unpatented), 'Kosi' (U.S. Ser. No. 09/145,546) and 'Himalaya' (U.S. Plant Pat. No. 10,935).

TABLE 1

Comparative performances of menthol mint strain 'Damroo' and three existing standard cultivars in Pilot Scale Trial conducted at Field Station Pantnagar (Plot Size: 16 m × 5 m).

| | Varieties/Strain | | | | |
|---|---|---|---|---|---|
| Characters | Shivalik | Himalaya | Kosi | Damroo | C.D. (5%) |
| Plant height (cm) | 95.5 | 122.1 | 122.7 | 104.2 | 4.13 |
| Length of leaf lamina (cm) | 7.3 | 7.6 | 7.4 | 7.5 | 0.25 |
| Leaf width (cm) | 4.5 | 4.2 | 3.3 | 4.6 | 0.32 |
| No. of leaves/ 3 aerial shoots | 147.3 | 156.4 | 165.5 | 161.2 | 7.61 |
| Leaf: Stem ratio | 0.75 | 0.94 | 1.31 | 0.90 | 0.065 |
| Days to maturity | 120–130 | 110–120 | 90–100 | 120–130 | — |
| Oil content (%) | 0.55 | 0.65 | 0.85 | 0.75 | 0.13 |
| Herbage yield/plot (kg) (6 m × 4 m) | 39.50 | 60.19 | 66.17 | 70.92 | 6.72 |
| Herbage yield/ha (g) | 164.6 | 250.8 | 275.7 | 295.5 | 3.10 |
| Oil yield/ha (kg) | 90.5 | 163.0 | 234.3 | 221.6 | 4.12 |
| Menthol content (%) | 70–75 | 75–78 | 78–80 | 75–78 | — |
| Seed yield/plant (g) | 1.0–2.0 | 0.7–1.2 | 1.0–1.5 | 1.0–3.0 | — |

TABLE 2

Comparative seed yield performances of 'Damroo,' and other 16 genotypes (13 selections + three controls) during 1998–99 at Pantnagar

| Genetic Stocks | DP | DH | Plant height (cm) | Seed yield/ha (kg) |
|---|---|---|---|---|
| Sel. 4-6-125 (Damroo) | Feb., 7 | June, 10 | 102.0 | 94.7 |
| Sel. 8-12-125 | Feb., 7 | June, 10 | 104.3 | 37.5 |
| Sel. 4-3-125 | Feb., 7 | June, 10 | 102.8 | 48.3 |
| Sel. 1-3-325 | Feb., 7 | June, 10 | 96.5 | 71.0 |
| Sel. 11-7-125 | Feb., 7 | June, 10 | 103.6 | 40.0 |
| Sel. 4-4-125 | Feb., 7 | June, 10 | 94.3 | 72.2 |
| Sel. 8-4-125 | Feb., 7 | June, 10 | 110.5 | 29.1 |
| Sel. 1-1-123 | Feb., 7 | June, 10 | 95.8 | 60.5 |
| Sel. 7-4-125 | Feb., 7 | June, 10 | 103.5 | 71.5 |
| Sel. 11-5-125 | Feb., 7 | June, 10 | 102.6 | 30.4 |
| Sel. 10-125 | Feb., 7 | June, 10 | 115.4 | 63.5 |
| Sel. 7-7-125 | Feb., 7 | June, 10 | 112.08 | 37.5 |
| Sel. 8-9-125 | Feb., 7 | June, 10 | 92.1 | 60.8 |

TABLE 2-continued

Comparative seed yield performances of 'Damroo,' and other 16 genotypes (13 selections + three controls) during 1998–99 at Pantnagar

| Genetic Stocks | DP | DH | Plant height (cm) | Seed yield/ha (kg) |
|---|---|---|---|---|
| Sel. 13-2-125 | Feb., 7 | June, 10 | 96.3 | 63.8 |
| Shivalik | Feb., 7 | June, 10 | 90.4 | 30.6 |
| Himalaya | Feb., 7 | June, 10 | 116.6 | 18.4 |
| Kosi | Feb., 7 | June, 10 | 118.3 | 29.5 |
| C.D. (5%) | — | — | 3.44 | 2.79 |

'Damroo' was vegetatively multiplied on a large scale during 1997–1998, to assess its productivity in PYT and PST. The PYT results clearly showed that the per hectare oil yield in 'Damroo,' besides being almost at par with that of 'Kosi' (U.S. Ser. No. 09/145,546) (221.6 kg against 234.3 kg of 'Kosi'), was much high over that of 'Himalaya' (U.S. Plant Pat. No. 10,935) (163.0 kg) and 'Shivalik' (unpatented) (90.5 kg). The PST results of assessment of 'Damroo' against the mentioned three standard varieties as well as the rest 13 seed producing selections for seed productivity are shown in Table 2. Per hectare seed yield in 'Damroo' was 94.7 kg as against 18.4 kg to 72.2 kg in the others. In order to have an understanding the potentiality of 'Damroo', as compared to the other varieties at both the crop levels: Main crop when grown during February–June and transplanted crops based on mature plants and seedlings and grown during April–July, we conducted another PST. It was evident that 'Damroo', besides registering per hectare oil yield, comparable with that of 'Kosi' (U.S. Ser. No. 09/145,546) in main cropping season (206.7 kg against 220.5 kg of 'Kosi'), retains its oil yield potential, even when grown as seedling-based transplanted crop. It came out as the best variety for exhibiting the maximum oil yield (200.1 kg against 70.5 kg to 150.3 kg of the others) in transplanted cropping season (Table 3).

TABLE 3

Comparative performances of menthol mint strain 'Damroo' and three exist standard cultivars in Pilot Scale Trial conducted at Field Station Pantnagar (Plot Size: 16 m × 5 m).

| Varieties/ Strain | Plant height (cm) | Herbage yield/ha (q) | Oil content (%) | Oil yield/ha (kg) | Oil production ration of transplanted crop and main crop (TC:MC) |
|---|---|---|---|---|---|
| Shivalik: MC (Feb.) | 94.3 | 164.00 | 0.55 | 90.2 | 0.78 |
| : TC (April) | 92.5 | 156.67 | 0.45 | 70.5 | |
| Himalaya: MC (Feb.) | 121.5 | 250.67 | 0.60 | 150.4 | 0.67 |
| : TC (April) (Mature plant) | 120.7 | 201.2 | 0.50 | 100.6 | |
| Kosi: MC (Feb.) | 122.1 | 275.62 | 0.80 | 220.5 | 0.68 |
| : TC (April) (Mature plant) | 120.5 | 231.23 | 0.65 | 150.3 | |
| Damroo: MC (Feb.) | 102.5 | 295.28 | 0.70 | 206.7 | 0.97 (TC raised by seedlings |
| : TC (April) (Seedling) | 102.3 | 333.50 | 0.60 | 200.1 | 0.39 |

TABLE 3-continued

Comparative performances of menthol mint strain 'Damroo' and three exist standard cultivars in Pilot Scale Trial conducted at Field Station Pantnagar (Plot Size: 16 m × 5 m).

| Varieties/ Strain | Plant height (cm) | Herbage yield/ha (q) | Oil content (%) | Oil yield/ha (kg) | Oil production ration of transplanted crop and main crop (TC:MC) |
|---|---|---|---|---|---|
| : TC (April) (Mature plant) | 101.6 | 160.60 | 0.50 | 80.3 | |
| C.D. (5%) for MC | 4.24 | 3.12 | 0.12 | 4.10 | |
| C.D. (5%) for TC | 4.18 | 3.08 | 0.11 | 5.21 | |

MC (Feb.): Main crop planted in February.
TC (April): Transplanted crop raised by mature plants (Mature plant) in the month of April.
TC (April): Transplanted crop raised by seedlings in the (seedling) month of April.

Essential oil samples, prepared from 'Damroo,' and the mentioned three control genotypes were examined by gas liquid chromatography (GLC). The oil content in 'Damroo' is higher (78 to 80%) in comparison to that in 'Shivalik' (unpatented) (70–75%) and 'Himalaya' (U.S. Plant Pat. No. 10,935) (75–78%) but is equal to that in 'Kosi' (U.S. Ser. No. 09/145,546) (78–80%).

Studies on disease resistance were conducted and the reactions of the new variety 'Damroo' as well as three control varieties: 'Shivalik' (unpatented), 'Himalaya' (U.S. Plant Pat. No. 10,935) and 'Kosi' (U.S. Ser. No. 09/145,546), to leaf spot, rust, powdery mildew, wilt, and root rot diseases under field conditions were scored during 1998–1999 (Planting date: 20th January) in CIMAP field Station Pantnagar. Leaf spot and rust scored on modified 9 point disease scale, where 1=0%, 2=1 to 5%, 3=6 to 10%, 4=11 to 20%, 5=21 to 30%, 6=31 to 40%, 7=41 to 60%, 8=61 to 80%, 9=81 to 100% foliage destroyed. Any variety was considered resistant, when it showed resistance on 1 to 3 in the scale. Powdery mildew scored a 1 to 5 on the scale and the variety scoring 0 to 1 was considered resistant. As to scoring in respect to wilt and root rot disease, reactions were found out on the basis of percent infected plants. Table 4 shows the results convincingly indicating relative resistance of the new variety 'Damroo' and the control 'Kosi' (U.S. Ser. No. 09/145,546).

TABLE 4

Comparative reaction of 'Damroo' and other three cultivars to, wilt and root rot disease, leaf spot rust, and powdery mildew disease.

| Name of the variety/genotype | Percent wilted plants after 80 days | Disease score (days after sowing) Leaf spot 40 | 60 | 80 |
|---|---|---|---|---|
| Shivalik | 10 | 1.7 | 4.2 | 5.8 |
| Himalaya | 02 | 1.0 | 1.2 | 1.8 |
| Kosi | Nil | 1.0 | 1.4 | 1.7 |
| Damroo | Nil | 1.0 | 1.0 | 1.2 |
| C.D. (5%) | — | 0.16 | 0.60 | 0.72 |

TABLE 4-continued

Comparative reaction of 'Damroo' and other three cultivars to, wilt and root rot disease, leaf spot rust, and powdery mildew disease.

| Name of the variety/genotype | Disease score (days after sowing) Rust 40 | Rust 60 | Rust 80 | Powdery mildew 40 | Powdery mildew 60 | Powdery mildew 80 |
|---|---|---|---|---|---|---|
| Shivalik | 2.0 | 4.1 | 5.9 | 00 | 0.1 | 0.7 |
| Himalaya | 1.0 | 1.0 | 1.0 | 00 | 0.4 | 0.7 |
| Kosi | 1.0 | 1.0 | 1.0 | 00 | 00 | 0.3 |
| Damroo | 1.0 | 1.0 | 1.0 | 00 | 00 | 0.3 |
| C.D. (5%) | 0.22 | 0.30 | 0.31 | 00 | 0.10 | 0.34 |

'Damroo' was further examined for its detailed cyto-chemo-taxonomical specificities. The corresponding results are as given below:

1. Genus: Mentha.
2. Sub-genus: Menthastnim.
3. Species: *arvensis L.*
4. Family: Lamiaceae.
5. Common name: Japanese mint/corn mint/menthol mint.
6. Plant:
   *Height.*—104.2±1.3 cm.
   *Width.*—47±20 cm.
7. Growth habit: Erect, vigorous with Pyramidal habit.
8. Stem: Round to quadrangular hard, woody, pubescent, yellowish green (144C), 7–9 mm thick at the internode.
9. Number of internodes: 28 to 35.
10. Length of internodes: 3.0 to 3.5 cm.
11. Leaf colour: Dark green (137 A) on upper surface. Dark green (137 A) to Green (137 C) on lower surface.
    *Texture.*—Moderately thick and rigid.
    *Surface.*—Slightly raised inbetween the veins, moderately hairy with glandular trichomes — on both sides— the ventral surface containing more trichomes.
    *Shape.*—Ovate at the beginning (until about 45 days after planting) and elliptic thereafter, compared to sustained elliptic growth in 'Himalaya,' 'Shivalik,' and 'Kosi'.
    *Margin.*—Shallow serration (38–64 number).
    *Tip.*—Acute.
    *Base.*—Attenuate.
    *Size.*—Moderately broad and long.
    *Petiole length.*—1.0–1.5 cm.
    *Area.*—14.0 $cm^2$.
    *Length.*—7.5 cm.
    *Width.*—4.6 cm, compared to 3.3 to 4.5 cm in 'Himalaya,' 'Shivalik,' and 'Kosi'.
12. Leaf: Stem ratio (w/w): 0.90.
13. Inflorescence: Verticillate (cymes). Each cyme comprises 26–28 as against 15 to 30 in 'Shivalik,' 'Himalaya,' and 'Kosi'; cymes occur in the leaf axils and form a whorl of florets around the stem.
14. Flowers (florets): Very small in size, perfect, hermaphrodite, nearly actinomorphic, and hypogynous.
    *Pedicel.*—1.5 to 2.5 mm in length, yellow green (154 C).
    *Calyx.*—Four sepals, persistent 2 to 3 mm in length, narrowly deltoid and acuminate, yellow green (145 B).
    *Corolla.*—White to Whitish-purple (76 D), 4.0 to 5.5 mm in length, composed of 4 petals, differentiated into tube and limb (tube due to fusion of the petals at their base).
    *Anthers.*—Four, ocidimetary, white, remain inside the corolla tube.
    *Stigma.*—Bifid, bicarpellary syncarpous; ovary superior, deeply fourlobed, bilocular, placentation exile, style gynobasic arising between the lobes of the ovary.
    *Fruit and seed.*—The fruit is of four one-seeded nutlets enclosed by the persistent calyx, the seed with a scanty endosperm and striate embryo. The seeds are brown, minute in size.
15. Underground: Profuse in number, faint purplish red (69 A) at the sucker apical Part.
16. Oil content in the fresh herb (%): 0.75 against 0.55, 0.65 and 0.85 of 'Shivalik,' 'Himalaya,' and 'Kosi,' respectively.
17. Oil quality:
    *Menthol content.*—78 to 80%.
    *Isomenthone content.*—12 to 17%.
    *Congealing point.*—2 to 21° C.

The new variety 'Damroo' is a herbaceous perennial with upright aerial shoots coming out of the underground suckers (rhizomes) growing laterally. The shoots grow erect, having branching with a special arrangement of branches giving a pyramidal look. The flowers are arranged in whorls and the inflorescence grows from the nodes at the leaf axil (FIG. 1). The chromosome number is 2n=12x=96 (octopliod). (The colour codes referred here are in accordance with The "R.H.S. colour chart" published by The Royal Horticultural Society, 80 Vincent Square, London SWIP 2PE, 1995).

Stability

'Damroo,' besides producing profuse homogenous seeds to facilitate the cultivation of mint as a transplanted crop, gives a high oil yield over all standard varieties in both a transplanted crop (April–July), as well as a main crop (February–June).

The plant has been cultivated and assessed for five years (1994–1999) and is found to be stable in producing homogenous seeds. Further, the plant has been tested continuously for two years and found that its essential oil yield is also consistent in two consecutive years (1997–1999) in various yield trails.

Statement of distinction

As evident from the morpho-physiology, new variety 'Damroo' is distinct from its mother variety as well as other existing varieties by having a new combination of plant traits. The pyramidal vigorous plant habit with dark green leaves, high yield, high oil yield, coupled with high methol content and capability in retaining homogeneity in population for plant traits, despite out-crossing within population in 'Damroo,' lead it to be a novel population-variety. High seed yielding ability is the major physiological "marker" for identifying 'Damroo,' from all the existing menthol mint varieties. The novelty of the invention is that 'Damroo', besides distinguishing it from the other varieties like 'Himalaya' (U.S. Plant Pat. No. 10,935) and 'Shivalik' (unpatented) in main cropping season by having oil productivity, distinctly out-classes all the standard varieties by possessing high oil productivity in transplanted mint cropping season. High seed productivity in 'Damroo' in particular, leads it to be the best variety for its meaningful uses as a potent seed source for raising much productive transplanted mint crop. To evolve a genotype having potentiality in giving profuse homogenous seeds even under cross pollination within its own plant population is a new finding in the world, where till date it is known that cross pollinated genotype gives only heterogeneous seeds.

'Damroo' gives about 94.7 kd seeds/hectare against only 30.5 kg of the familiar variety 'Shivalik' (unpatented). 'Damroo,' when grown as transplanted mint through its homogenous seed, gives about 200 kg essential oil/hectare against about 70.5 kg of oil/hectare in the widely cultivated variety 'Shivalik' (unpatented).

In short, the present invention provides a novel *Mentha arvensis* mint population variety 'Damroo' characterized for its sustained high potentiality of reproducing viable seeds and phenotypically homogenous seed-derived plant population under out-crossing, and facilitating for economically viable transplanted menthol mint cropping to avoid the cultivation of menthol mint in place of staple cereal wheat.

We claim:

1. A new and distinct cultivar of *Mentha arvensis* plant named 'Damroo,' substantially as herein illustrated and described, having the following characteristics:

(a) dark greenish leaves (137A), white to whitish purple (76D) petals, and branching providing a pyramidal habit;
(b) tolerance to leaf spot, rust, and powdery mildew;
(c) essential oil containing 78–80% menthol and 12–17% isomenthone;
(d) seed yields in the range of about 90–96kg/hectare; and,
(e) the capacity to retain homogeneity of plant traits, despite out-crossing within the population.

* * * * *